(12) United States Patent
Hussein

(10) Patent No.: US 6,556,653 B2
(45) Date of Patent: Apr. 29, 2003

(54) NON-ROTATING X-RAY SYSTEM FOR THREE-DIMENSIONAL, THREE-PARAMETER IMAGING

(75) Inventor: Esam Hussein, Fredericton (CA)

(73) Assignee: University of New Brunswick, Fredericton (CA)

(*) Notice: Subject to any disclaimer, the term of this patent is extended or adjusted under 35 U.S.C. 154(b) by 24 days.

(21) Appl. No.: 09/860,538

(22) Filed: May 21, 2001

(65) Prior Publication Data

US 2001/0046275 A1 Nov. 29, 2001

Related U.S. Application Data

(60) Provisional application No. 60/206,803, filed on May 25, 2000.

(51) Int. Cl.[7] .................. G01N 23/201; G01N 23/04
(52) U.S. Cl. ..................... 378/90; 378/57; 378/86; 378/87; 378/88; 378/89
(58) Field of Search ............... 378/86, 87, 88, 378/89, 90, 57

(56) References Cited

U.S. PATENT DOCUMENTS

| | | | |
|---|---|---|---|
| 4,123,654 A | 10/1978 | Reiss et al. | 378/87 |
| 4,228,351 A | 10/1980 | Snow et al. | 378/54 |
| 4,423,522 A | 12/1983 | Harding | 378/87 |
| 4,768,214 A | 8/1988 | Bjorkholm | 378/87 |
| 4,785,401 A | 11/1988 | Harding et al. | 378/87 |
| 4,799,247 A | 1/1989 | Annis et al. | 378/87 |
| 4,850,002 A | 7/1989 | Harding et al. | 378/87 |
| 4,870,670 A | 9/1989 | Geus | 378/87 |
| 4,884,289 A | 11/1989 | Glockmann et al. | 378/57 |
| 4,887,285 A | 12/1989 | Harding et al. | 378/88 |
| 4,896,342 A | 1/1990 | Harding | 378/87 |
| 4,956,856 A | 9/1990 | Harding | 378/88 |
| 5,023,895 A | 6/1991 | McCroskey et al. | 378/4 |
| 5,033,073 A | 7/1991 | Friddell | 378/146 |

(List continued on next page.)

FOREIGN PATENT DOCUMENTS

| | | |
|---|---|---|
| CA | 1101133 | 5/1981 |
| CA | 1135878 | 11/1982 |
| CA | 1157968 | 11/1983 |
| CA | 2243629 | 8/1997 |

OTHER PUBLICATIONS

Harding, G. and Kosanetzky, J, "Scattered X–ray Beam Nondestructive Testing", Nuclear Instruments and Methods, vol. A280, pp. 517–528, 1989.

Prettyman, T.H., Gardner, R.P., Russ, J.C. and Verghese, K., "A Combined Transmission and Scattering Tomographic Approach to Composition and Density Imaging", Applied Radiation and Isotopes, vol. 44, pp. 1327–1341, 1993.

(List continued on next page.)

Primary Examiner—Drew A. Dunn
Assistant Examiner—Allen C. Ho
(74) Attorney, Agent, or Firm—Mario Theriault

(57) ABSTRACT

The system for inspecting an object comprises a structure having a first, second and third orthogonal axes, and a source of x-ray pencil beam mounted thereto along the first axis. An incident radiation detector is mounted to the structure perpendicularly to the first axis. A first and second linear arrays of scattered radiation detectors are mounted to the structure perpendicularly to the second and third axes respectively. The source of x-ray pencil beam, the incident radiation detector and the first and second linear arrays of scattered radiation detectors are spaced apart and define therebetween an inspection zone. In use, an object to be inspected is moved inside the inspection zone relative to the x-ray pencil beam. The object is inspected voxel by voxel and the radiation measurements taken at each voxel are indicative of incident radiation attenuation, scattered radiation attenuation and electron density of that voxel.

5 Claims, 2 Drawing Sheets

U.S. PATENT DOCUMENTS

| | | | |
|---|---|---|---|
| 5,040,200 A | 8/1991 | Ettinger et al. | 378/88 |
| 5,070,455 A | 12/1991 | Singer et al. | 378/6 |
| 5,125,015 A * | 6/1992 | Shimoni et al. | 378/51 |
| 5,179,581 A | 1/1993 | Annis | 378/57 |
| 5,247,560 A | 9/1993 | Kotowski | 378/54 |
| 5,247,561 A | 9/1993 | Kotowski | 378/87 |
| 5,260,982 A | 11/1993 | Fujii et al. | 378/87 |
| 5,313,511 A | 5/1994 | Annis et al. | 378/87 |
| 5,367,552 A | 11/1994 | Peschmann | 378/57 |
| 5,420,905 A | 5/1995 | Bertozzi | 378/88 |
| 5,428,657 A | 6/1995 | Papanicolopoulos et al. | 378/86 |
| 5,430,787 A | 7/1995 | Norton | 378/87 |
| 5,524,133 A | 6/1996 | Neale et al. | 378/53 |
| 5,533,080 A | 7/1996 | Pelc | 378/5 |
| 5,590,169 A | 12/1996 | Monteiro | 378/87 |
| 5,600,700 A | 2/1997 | Krug et al. | 378/57 |
| 5,642,393 A | 6/1997 | Krug et al. | 378/57 |
| 5,642,394 A | 6/1997 | Rothschild | 378/57 |
| 5,684,857 A | 11/1997 | De Bokx | 378/45 |
| 5,692,029 A | 11/1997 | Husseiny et al. | 378/88 |
| 5,696,806 A | 12/1997 | Grodzins et al. | 378/86 |
| 5,703,923 A | 12/1997 | Bardash | 378/87 |
| 5,729,582 A | 3/1998 | Haw et al. | 378/89 |
| 5,838,758 A | 11/1998 | Krug et al. | 378/53 |
| 5,930,326 A | 7/1999 | Rothschild et al. | 378/57 |
| 5,940,468 A | 8/1999 | Huang et al. | 378/57 |
| 5,970,116 A | 10/1999 | Dueholm et al. | 378/90 |
| 5,974,111 A | 10/1999 | Krug et al. | 378/57 |
| 6,018,562 A | 1/2000 | Willson | 378/9 |
| 6,052,433 A | 4/2000 | Chao | 378/98.9 |
| 6,151,381 A * | 11/2000 | Grodzins et al. | 378/90 |
| 6,175,116 B1 * | 1/2001 | Gagnon et al. | 250/363.03 |
| 6,327,546 B1 * | 12/2001 | Petrillo et al. | 702/89 |
| 6,442,233 B1 * | 8/2002 | Grodzins et al. | 378/57 |

OTHER PUBLICATIONS

Arendtsz, N., V. and Hussein E.M.A., "Energy–spectral Scatter Imaging. Part I: Theory and Mathematics", IEEE Transactions on Nuclear Science, vol. 42, pp. 2155–2165, 1995.

Arendtsz, N., V. and Hussein E.M.A., "Energy–spectral Scatter Imaging. Part II: Experiments", IEEE Transactions on Nuclear Science, vol. 42, pp. 2166–2172, 1995.

MCNP 4C, Monte Carlo N–Particle Transport Code System, RSICC Code Package CCC–700, Oak Ridge National Laboratory.

Glasstone S. and Sesonske, A., Nuclear Reactor Engineering, Chapter 2, Chapman & Hall, New York, 1994.

Zieglier, C.A., Bird, L.L. and Chelčk, "X–Ray Raleigh Scattering Method for Analysis of Heavy Atoms in Low Z Media", Analytical Chemistry, vol. 13, pp. 1794–1798, 1956.

Bray, D.E. and Stanley, R.K., Nondestructive Evaluation, Chapter 20, McGraw–Hill, New York, 1989.

Battista, J.J. and Bronskill, M.J., "Compton scatter imaging of transverse sections: and overall appraisal an evaluation for radiotherapy planning", Physics in Medicine and Biology, vol. 26, pp. 81–99, 1981.

Lale, P.G., "The examination of internal tissues, using gamma–ray scatter with a possible extension to megavoltage radiography", Physics in Medicine and Biology., vol. 4, pp. 159–167, 1959.

Hussein, E.M.A., "Compton Scatter Imaging Systems", in Bioinstrumentation: Research, Development and Applications, Butterworths Publ., Stoneham, MA, D.L. Wise, Ed., Chapter 35, pp. 1053–1086, 1990.

* cited by examiner

NON-ROTATING X-RAY SYSTEM FOR THREE-DIMENSIONAL, THREE-PARAMETER IMAGING

This application claims the benefit of Provisional application Ser. No. 60/206,803, filed May 25, 2000.

This invention was made with Government support under Research Grant # 97-G-029 awarded by the Federal Aviation Administration. The Government has certain rights in this invention.

FIELD OF THE INVENTION

This invention relates to X-ray imaging systems, and more particularly the present invention relates to composition, density and geometry imaging of an object by measuring and analyzing incident and scattered radiation passing through that object.

BACKGROUND OF THE INVENTION

The following publications relate to the subject of x-ray imaging systems and methods. Various teachings from these publications are cited herein to facilitate the description of the present invention.

Glasstone S. and Sesonske, A., Nuclear Reactor Engineering, Chapter 2, Chapman & Hall, New York, 1994.

Zieglier, C. A., Bird, L. L. and Chelek, "X-Ray Raleigh Scattering Method for Analysis of Heavy Atoms in Low Z Media", Analytical Chemistry, Vol. 13, pp. 1794–1798, 1956.

Bray, D. E. and Stanley, R. K., Nondestructive Evaluation, Chapter 20, McGraw-Hill, New York, 1989.

Battista, J. J. and Bronskill, M. J., "Compton scatter imaging of transverse sections: an overall appraisal and evaluation for radiotherapy planning", Physics in Medicine and Biology, Vol. 26, pp. 81–99, 1981.

Lale, P. G., "The examination of internal tissues, using gamma-ray scatter with a possible extension to megavoltage radiography", Physics in Medicine and Biology., Vol. 4, pp. 159–167, 1959.

Hussein, E. M. A., "Compton Scatter Imaging Systems", in Bioinstrumentation: Research, Development and Applications, Butterworths Publ., Stoneham, M A, D. L. Wise, Ed., Chapter 35, pp. 1053–1086, 1990.

Harding, G. and Kosanetzky, J, "Scattered X-ray Beam Nondestructive Testing", Nuclear Instruments and Methods, Vol. A280, pp. 517–528,1989.

Prettyman, T. H., Gardner, R. P., Russ, J. C. and Verghese, K., "A Combined Transmission and Scattering Tomographic Approach to Composition and Density Imaging", Applied Radiation and Isotopes, Vol. 44, pp. 1327–1341, 1993.

Arendtsz, N., V. and Hussein E. M. A., "Energy-spectral Scatter Imaging. Part I: Theory and Mathematics", IEEE Transactions on Nuclear Science, Vol. 42, pp. 2155–2165, 1995.

Arendtsz, N., V. and Hussein E. M. A., "Energy-spectral Scatter Imaging. Part II: Experiments", IEEE Transactions on Nuclear Science, Vol. 42, pp. 2166–2172, 1995.

MCNP 4C, Monte Carlo N-Particle Transport Code System, RSICC Code Package CCC-700, Oak Ridge National Laboratory.

Conventional x-ray radiographic systems, commonly used in airports to detect weapons, sharp objects and the likes, are not suited for the detection of plastic explosives. This is due to the fact that such systems typically utilize low-energy photons, where the photoelectric effect (photon absorption) dominates. The probability of photoelectric absorption per atom can be roughly expressed as follows as taught by Glasstone et al.:

$$\tau \approx \text{constant } Z^n/E^3 \quad (1)$$

where Z is the atomic number of the medium, E is the photon energy, and the exponent n varies between 3 for low-energy photons to 5 for high-energy rays. Therefore, the low Z-number of nitrogen-based explosives makes it difficult to distinguish them from other common materials, with the photoelectric effect on which conventional radiography relies. Alternative techniques were therefore developed.

If the Compton scattering modality of photons is allowed to come into play, then additional information can be brought in to assist in detecting explosives. The probability of Compton scattering per atom, $\sigma$ depends on the number of electrons available as scattering targets and therefore increases linearly with Z, and can be expressed as follows, as taught by Glasstone et al.

$$\sigma = \text{constant } Z/E \quad (2)$$

Therefore, Compton scattering provides density-related information. The electron density is directly proportional to Z, and the mass density is proportional to the electron density (given that the ratio of the atomic-number to the mass-number is equal to about one-half for most elements, except hydrogen) as taught by Zieglier et al.

Compton scattering can provide such mass-density information, which if used in conjunction with the Z-number information given by the photoelectric effect can help in identifying nitrogen-based explosives; that are characterized by having higher mass density than most common organic materials. A dual-energy (high and low) radiographic system can be used for this purpose; with the higher energy providing electron-density information and the lower energy strongly reflecting the effect of the Z-number, according to equations (1) and (2). This is the concept of the E-scan system. Alternatively, scattering can be monitored, typically back scattering, to obtain density information.

Another useful photon-interaction modality is the coherent Rayleigh scattering process, where photons are deflected by a small angle without losing energy. The probability of this reaction is however small and is proportional to $Z^3$ making the reaction more sensitive to metals, as taught by Zieglier et al.

X-ray fluorescence depends on the production of x-rays characteristic of the target atom. However the technique is best suited for high Z atoms, and even then the measured flux is low, as taught by Zieglier et al.

The remaining photon interaction of significance is pair production, where a high energy photon disintegrates into an electron-positron pair in the presence of the electromagnetic field of the atom. Once again, this is an interaction that dominates at high Z number and high photon energy, as taught by Glasstone et al. This leaves the photoelectric effect and Compton scattering as the most suitable photon-interaction modalities for use in imaging.

Radiography techniques are disadvantaged by the fact that they provide integrated information, along the chord of radiation transmission, thus mixing the attributes of overlying objects. This can lead to masking and smearing out of information. Computed tomography (CT) solves this problem by unfolding the radiation-attenuation measurements into pixel-specific information at individual slice of the object. While solving the masking problem of radiography, the fact still remains that CT determines the attenuation coefficient of the material present in the pixel. Therefore, at the commonly used X-ray operating range of 80–200 kV, keeping in mind that the average X-ray energy in keV is equal to about one-third the peak energy which corresponds to the operating voltage in kV as taught by Bray et al., the photoelectric effect dominates in CT, as can be seen by comparing the equations (1) and (2). Therefore, in essence one obtains physical information that is identical in nature to that obtained by basic radiography, although de-convoluted into individual pixels. This comes at considerable cost due to the involvement of a complex mechanical scanning mechanism and a sophisticated numerical image reconstruction process.

The question now is whether a material can be uniquely identified from the value of its attenuation coefficient, or CT number. This question has bewildered medical physicists who plan for radiotherapy (at high photon-energy where Compton-scattering is dominant) from CT images (produced by low-energy X-rays where the photoelectric effect prevails). With the known nature of the body, some empirical formulations are devised, relating CT numbers to the electron density of tissue, muscles and bones, as taught by Battista et al. Given however the wide variety of materials that may be present in a passenger luggage, CT numbers may not necessarily be uniquely related to density, thus resulting in ambiguous and perhaps false indications. Like the case with conventional radiography, more information is needed to uniquely identify an explosive material from CT images. Such information can come from a suspicious object geometry, or other non-technical supplementary information. Alternatively, one can expect CT to progress in the same fashion as conventional radiography to provide additional physical information.

Progress of CT as an explosive detection system (EDS) requires that it provides both density and Z-number information. This can be achieved, similar to E-scan, by using a dual-energy CT system; but this duplicates an already mechanically and numerically intensive process. Alternatively, one can rely on combination of scattering and transmission measurements to provide electron-density and Z-number information. Scattering can also enable the development of a simplified and less expensive (non-rotating) imaging system; which is more suited for imaging carry-on luggage and/or for use in small and remote airports where the cost of a CT system can be prohibitive. Rotation-scanning is also more difficult to perform on bulky objects, such as cargo containers; and hence there is a need for non-rotating imaging system.

A brief review of Compton-scatter imaging (CSI) is given hereinbelow to further facilitate the description of the present invention.

Scatter imaging resembles the natural imaging process in which the naked-eye constructs an image from light reflected off the surface of an object. Unlike light, radiation penetrates deep into the object enabling volume imaging. Imaging underneath a surface is complicated however by the attenuation of radiation prior to and following scattering. This attenuation effect complicates the imaging process and has hindered the progress of scatter imaging for many years. The history of imaging with scattered photons can be traced back to the work of Lale in 1959, who employed a high-energy source, and consequently ignored altogether the attenuation effect. Many other workers attempted to overcome this problem in a variety of ways, for example Hussein. Perhaps the most significant developments in CSI are those of Battista et al., Prettyman et al., Harding et al., and Hussein & Arendtsz, which are briefly described below.

Battista et al. employed a gamma-ray source and a rectilinear scanning process, which enabled the determination of each pixel's density as the scanning process progressed. The density of a preceding pixel was used to calculate the attenuation coefficients of the subsequent pixel. The ComScan™ system of Harding et al. utilizes a collimated X-ray source and a detector array equipped with pinhole-type collimator to measure back scattered radiation. No correction for radiation attenuation appears to be incorporated in ComScan™, making the system suitable only for 'imaging of superficial regions of massive objects'. Prettyman et al. used gamma rays and employed a combination of tomographic transmission scanning and projected Compton scatter imaging to obtain composition (Z-number) and density images. This system, however, relied on a scanning/rotation process that involved a large number of projections. In the recent work of Arendtsz and Hussein, the scanning process was avoided altogether by measuring the energy of the scattered photons and relating it to the angle of scattering using the unique energy-to-angle relationship of single-collision Compton scattering. A gamma-ray source was used to provide a mono-energetic source, thus facilitating the process of relating the energy to the angle of scattering. An iterative image reconstruction process was employed by Arendtsz and Hussein to overcome the nonlinear problem of accounting for pre- and post-scattering attenuation.

SUMMARY OF THE INVENTION

The present invention consists of a non-rotating photon (X-ray) system and methods for three-dimensional, three-parameter imaging of objects, for the purpose of identifying non-intrusively their material content. This system and methods are useful, for instance, in detecting explosives, narcotics, or other contraband materials, in passenger luggage or shopped parcels. The system and methods provide simultaneously three independent physical properties that enables the classification of materials by density and overall composition, in addition to the shape information provided by a 3-D imaging process. The system and methods employ a collimated beam of photons emitted from an x-ray machine operating in the 300 to 400 kV range, and monitor radiation scattered to the sides of the object, along with transmitted radiation. A rectilinear scanning process moves the object in front of the radiation beam in small steps, until the entire object is covered with radiation, by penetration through only one of its surface (that facing the source).

This scanning process simplifies the imaging process and reduces its cost relative to conventional systems, by enabling the source and detectors to be fixed in place. The scanning process facilitates the use of a single transmission detector, and one-dimensional (line) arrays of scattering detectors. It also renders the imaging process into a simple point-by-point imaging process, wherein the measurements are readily mathematically formulated and numerically processed to reconstruct simultaneously three images: a) the radiation attenuation coefficient at the source energy, b) the attenuation coefficient at the scattering energy, and c) the electron density at each voxel. The difference in photon energy between the incident and the scattered photons makes the attenuation coefficient for the latter more sensitive to variations in the atomic number of the material than the attenuation coefficient at the incident energy. Therefore, this invention is unique in its tri-property imaging process; a feature not provided by any other imaging systems, and should provide higher confidence in detecting concealed objects.

One feature of the present invention is that it advances the progression of X-ray explosive detection systems (EDS) by developing a Compton-scatter/transmission system which provides both density and atomic-number images of scanned objects. The system and methods according to the present invention are particularly appropriate for luggage imaging whereby density, attenuation-coefficient and atomic-number images, are obtained in a manner that requires exposing the luggage to radiation from only one side thereof, thus eliminating the need for a rotating scanning mechanism. This is done by combining the best features of various Compton-scatter-imaging approaches into a system suitable for luggage imaging while employing the rectilinear scanning process of Battista et al.; a source-detector arrangement similar to that of Harding et al. ; single-projection transmission measurements to provide density and Z-number information in a manner similar to that of Prettyman et al., and simplified forms of the mathematical formulations and image reconstruction algorithms as taught by Arendtsz & Hussein.

By eliminating the source/detector, or object, rotation process of transmission CT systems, a simplified system has been developed, with decreased mathematical and numerical complexity. The system and methods according to the present invention should enable more wide-spread installation of EDS in airports. The simplification process comes at the added advantage of supplying not only attenuation coefficients (CT numbers), but also providing atomic-number information (through the ratio of the attenuation coefficient of the photoelectric effect to that of Compton scattering), as well as atomic number images (through Compton scattering). This is in addition to the spatial imaging information that can enable the identification of the geometry of a concealed object. With a sufficiently small voxel size, the method may also enable the detection of sheets of explosives. The system and methods according to the present invention advance CT technology in the same way radiographic technology progressed, through the E-scan and back scattering concepts, to meet the demands of explosive detection.

Broadly, in accordance with one aspect of the present invention, there is provided a system for inspecting an object, comprising; a structure having a first, second and third orthogonal axes, and a source of collimated x-ray pencil beam mounted thereto along the first axis. The system also comprises an incident radiation detector mounted to the structure perpendicularly to the first axis; a first linear array of scattered radiation detectors mounted to the structure perpendicularly to the second axis, and a second linear array of scattered radiation detectors mounted to the structure perpendicularly to the third axis. The source of collimated x-ray pencil beam, the incident radiation detector and the first and second linear arrays of scattered radiation detectors being spaced apart and defining therebetween an inspection zone. The system according to the present invention further has means for moving an object to be inspected, relative to the source of collimated x-ray pencil beam, mounted to the structure in the inspection zone.

This system is particularly advantageous for being relatively simple and wherein the radiation measurements available therefrom when inspecting a voxel in an object are indicative of incident radiation attenuation, scattered radiation attenuation and electron density of that voxel.

In accordance with another aspect of the present invention, there is provided a method for inspecting an object. This method comprises the steps of: defining and associating a first and second orthogonal axes with an object to be inspected; defining a voxel in that object; passing a x-ray beam through that voxel along the first axis, and measuring incident radiation attenuation through the voxel along the first axis. While maintaining the x-ray beam aligned along the first axis, passing the x-ray beam through the object alongside the voxel and measuring scattered radiation attenuation through the voxel along the second axis. A final step consists of relating the measured incident radiation attenuation and the measured scattered radiation attenuation to a material property of the voxel.

This method is particularly advantageous because the measured incident and scattered radiation attenuations and the related material property are representative of an entirety of the voxel. The scanning of an object using this method can be done broadly, with few measurements and large voxels for example, and still provide reliable information as to the content of each voxel.

In accordance with a further aspect of the present invention, there is provided a method for inspecting an object, and which comprises the steps of: defining and associating a first, second and third orthogonal axes with an object to be inspected; defining a voxel in that object, and passing a x-ray beam through the voxel along the first axis. The method also comprises the steps of: measuring incident radiation attenuation through the voxel along the first axis; measuring scattered radiation through the voxel along the second axis, and measuring scattered radiation through the voxel along the third axis. Further steps are: using the measured scattered radiation along the second and third axes, verifying the incident radiation attenuation along the first axis, and extracting volume imaging characteristics of that voxel from the measured radiation attenuations along the three axes.

This second method provides volume imaging characteristics along three orthogonal axes without rotating the object. These characteristics are particularly advantageous for generating 3D images of structural details inside each voxel.

Other advantages and novel features of the present invention will become apparent from the following detailed description.

BRIEF DESCRIPTION OF THE DRAWINGS

One embodiment of this invention is illustrated in the accompanying drawings in which.

DETAILED DESCRIPTION OF THE PREFERRED EMBODIMENT

Figure 1:
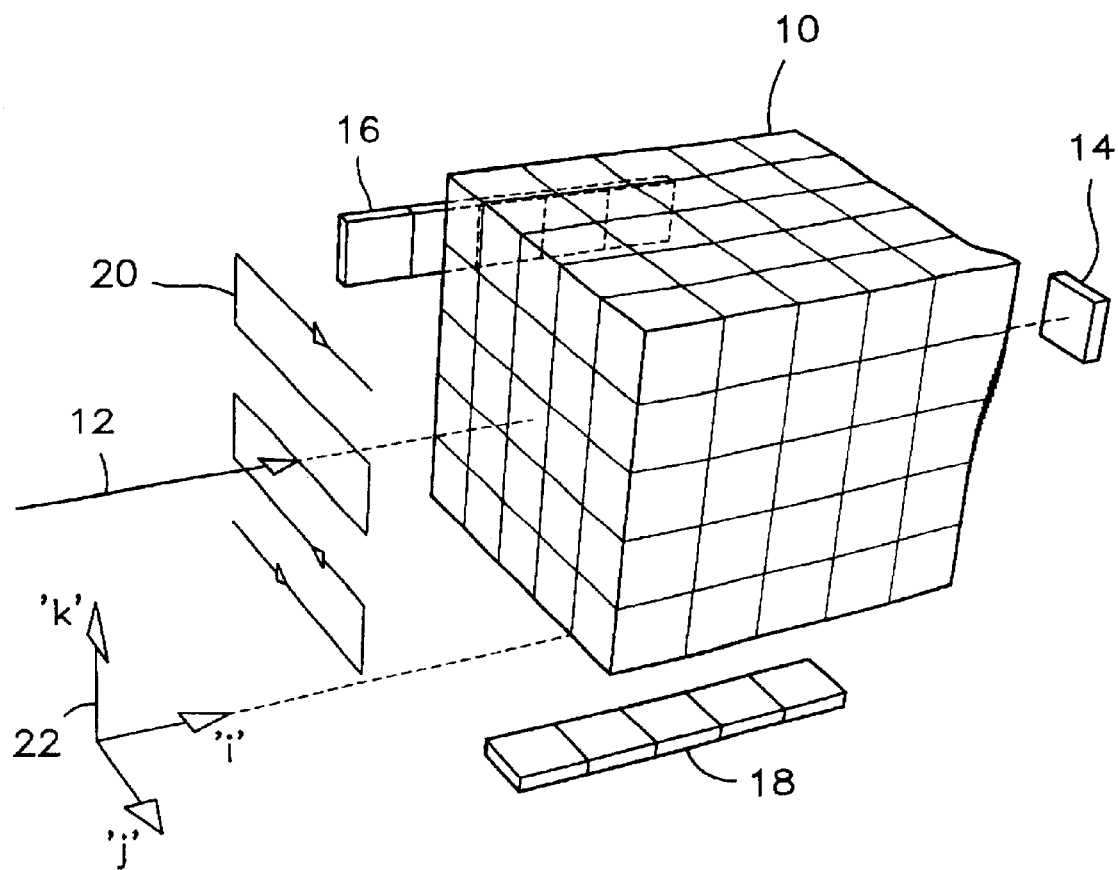
FIG. 1 is a schematic illustration of the scanning system and process.

While this invention is susceptible of embodiments in many different forms, there is shown in the drawings and will be described in details herein a specific embodiment, with the understanding that the present disclosure is to be considered as an example of the principles of the invention and is not intended to limit the invention to the embodiment illustrated and described.

The system according to the preferred embodiment is shown schematically in FIG. 1. A pencil beam of photons is made incident on the object, while the transmitted photons and photons scattered by 90-degrees are monitored by bottom detectors and side detectors. The beam is moved in a rectilinear manner as shown in the FIG. 1, so that one row of voxels is monitored at a time. Each detector is to be collimated such that it sees only photons incident normal to its surface.

Figure 2:
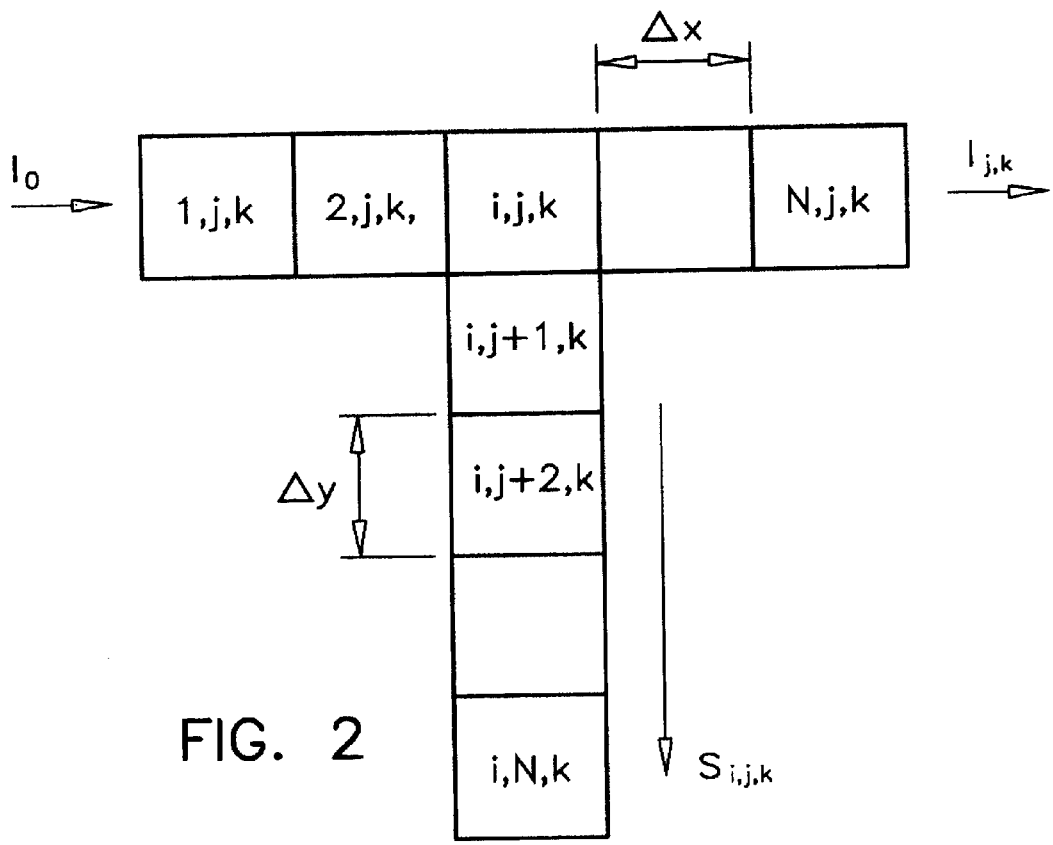
FIG. 2 illustrates the radiation path to the side detectors.
Figure 3:
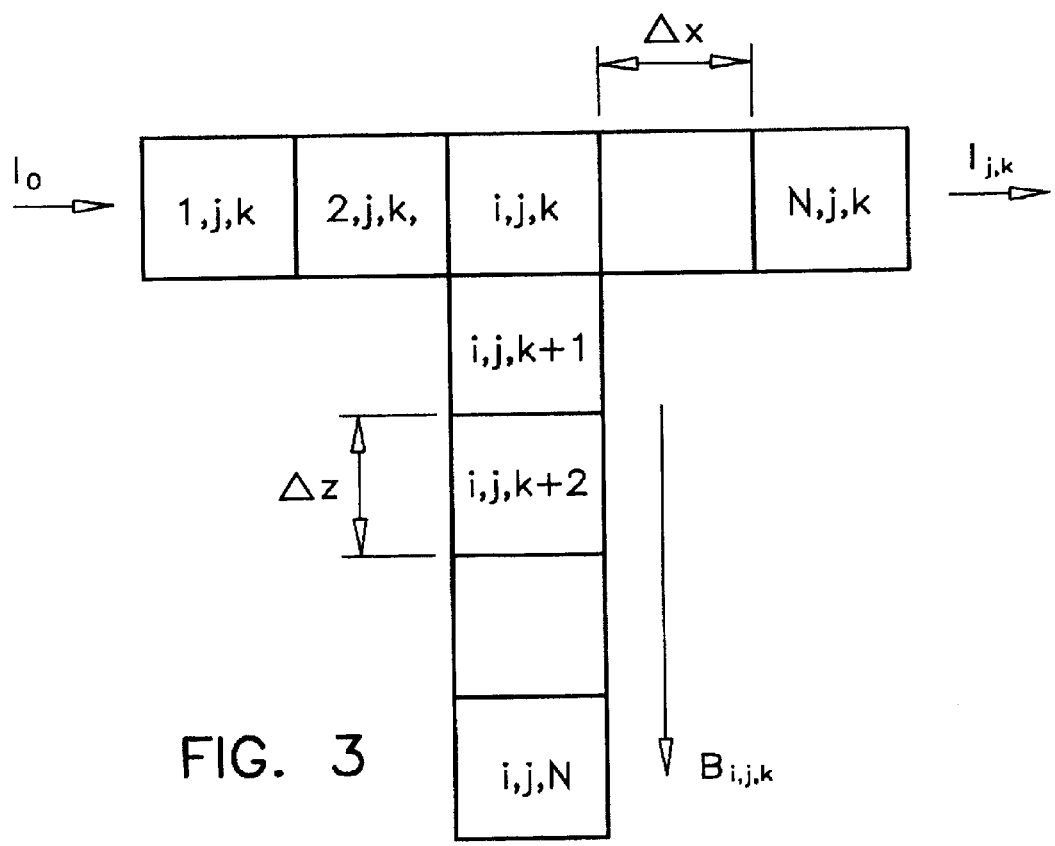
FIG. 3 illustrates the radiation path to the bottom detectors.

In the illustration of FIG. 1, the label 10 shows the test object to be scanned. The numeral 12 designates the incident x-ray beam. Numerals 14, 16 and 18 designate the incident radiation detector, the side array of scattered radiation detectors and the bottom array of scattered radiation detectors, respectively. Numeral 20 indicates the direction of movement of the x-ray beam during the scanning of the test object, and numeral 22 denotes an orthogonal coordinate symbol in which the vectors indicate the reference axes 'i', 'j' and 'k'. In FIGS. 2 and 3, the incident x-ray beam is shown as $I_0$. The incident radiation through one of the voxel is shown as $I_{j,k}$. The side scattering radiation is shown as $S_{i,j,k}$, and the bottom scattering radiation is shown as $B_{i,j,k}$.

Positioning detectors at the bottom of the luggage may be avoided by locating the detectors at the top. It is also possible to place detectors on both sides of the object, to duplicate the number of measurements. A fixed-array of scattering detectors can be used, or a single-row of detectors, as shown, can be employed and moved to match the position of the source. Similarly, a single-transmission mobile detector, aligned with the incident beam, can be employed, or a fixed array of detectors can be used. Preferably, the incident beam and all detectors are fixed, and the object is moved across the x-ray beam. This flexibility is one advantage of the system and methods according to the present invention. Therefore, the movement of the x-ray beam or of the object being inspected, as mentioned throughout the present disclosure should be considered as being a relative movement between the object and the x-ray beam.

Consider an object fictitiously divided to N×N×N voxels. Consider the (j, k)th incident beam, i.e. the beam directed through the voxels at the (j, k)th row of voxels. When this row of voxels is exposed to radiation, it contributes to the (j, k)th transmission detector measurement, to N scattering side detector measurements at level k and to N scattering bottom detector measurements at row j, as schematically shown in FIGS. 2 and 3. The response of each detector can be mathematically expressed as follows:

For Transmission:

$$I_{j,k} = I_0 \exp[-\Sigma^N_{i=1} \mu_{i,j,k} \Delta x] \quad (3)$$

For Side scattering:

$$S_{i,j,k} = S^0_{i,j,k} \exp[-\Sigma^{i-1}_{m=1} \mu_{m,j,k} \Delta x] \{\rho_{i,j,k}\} \exp[-\Sigma^N_{n=j+1} \mu'_{i,n,k} \Delta y]; i=1 \text{ to } N \quad (4)$$

For Bottom Scattering:

$$B_{i,j,k} = B^0_{i,j,k} \exp[-\Sigma^{i-1}_{m=1} \mu_{m,j,k} \Delta x] \{\rho_{i,j,k}\} \exp[-\Sigma^N_{n=k+1} \mu'_{i,j,n} \Delta z]; i=1 \text{ to } N \quad (5)$$

where $I_0$ is the intensity of the incident radiation, $S^0_{i,j,k}$ and $B^0_{i,j,k}$ are system constants that depend on the intensity of the incident beam, the probability of scattering, detector efficiency and system geometry, as well as the relative position of the voxel to the detector in case of scattering; $\mu$ is the attenuation coefficient of the incident radiation and $\mu'$ is that of the scattered photons; $\rho$ is the electron density of the voxel; and $\Delta x$, $\Delta y$ and $\Delta z$ are the dimensions of the voxel in the i, j and k directions, respectively. Note that self-attenuation (i.e. within voxel attenuation) is neglected, assuming that the voxel's volume is sufficiently small.

For the (1,1) beam, i.e. the beam at bottom of the test object and closest to the side-scattering detectors, equations (3) to (5) become:

$$I_{1,1} = I_0 \exp[-\Sigma^N_{i=1} \mu_{i,1,1} \Delta x] \quad (6)$$

$$B_{1,1,1} = B^0_{1,1,1} \{\rho_{1,1,1}\} \quad (7)$$

$$B_{2,1,1} = B^0_{2,1,1} \exp[-\mu_{1,1,1} \Delta x] \{\rho_{2,1,1}\} \quad (8)$$

$$B_{3,1,1} = B^0_{3,1,1} \exp[-(\mu_{1,1,1} + \mu_{2,1,1}) \Delta x] \{\rho_{3,1,1}\} \quad (9)$$

$$B_{N,1,1} = B^0_{N,1,1} \exp[-\Sigma^{N-1}_{i=1} \mu_{i,1,1} \Delta x] \{\rho_{N,1,1}\} \quad (10)$$

The first bottom-scattering measurement gives directly an estimate of $\rho_{1,1,1}$. If the source energy is sufficiently high, so that Compton scattering dominates, $\mu$ is linearly proportional to $\rho$, say $\mu = \sigma_0 \rho$ with $\sigma_0$ being a pre-set estimated constant, then one can estimate $\mu_{1,1,1}$ knowing $\rho_{1,1,1}$. The second side-scattering equation gives an estimate of $\rho_{2,1,1}$. One can then proceed sequentially to determine the $\rho$'s of the other voxels along the beam from the subsequent equations. Now, having an estimate of all $\rho$'s, and an estimate of the summation of all $\mu$'s from the transmission measurement, equation (6), one can obtain a new estimate of the constant $\sigma_0$ and update the estimates of $\rho$'s. This process should converge rapidly if Compton scattering is dominant, since the original value of $\sigma_0$ should provide a good estimate. Note that since self-attenuation is ignored, for the (1,1)th beam, side-scattering provides information similar to that of bottom-scattering, and the average of the two can be used to provide a better estimate.

Now, let us move the x-ray beam to the second position (2,1), i.e. keep the beam closest to the bottom detectors and move one voxel-width away from the side detectors. With self-attenuation ignored, the bottom-scattering detectors provide estimates of the $\rho$'s across this second row of voxels. The response of the side-scattering detectors contains, however, the attenuation coefficients of the voxels in the first row, $\mu'$'s, at the energy of scattering. Since this energy is lower than the incident energy, and if the energies are carefully selected so that the photoelectric effect dominates at the scattering energy, then $\mu'$ becomes a strong function of Z, equation (1), providing atomic number information. The values of $\mu'$'s for the first row of voxels can be calculated from the response of the side-scattering detectors as follows:

$$S_{1,2,1} = S^0_{1,2,1} \{\rho_{1,2,1}\} [-\mu'_{1,1,1} \Delta y] \quad (11)$$

$$S_{2,2,1} = S^0_{2,2,1} \exp[-\mu_{1,2,1} \Delta x] \{\rho_{2,2,1}\} \exp[-\mu'_{2,1,1} \Delta y] \quad (12)$$

$$S_{3,2,1} = S^0_{3,2,1} \exp[-(\mu_{1,2,1} + \mu_{2,2,1}) \Delta x] \{\rho_{3,2,1}\} \exp[-\mu'_{3,1,1} \Delta y] \quad (13)$$

$$S_{N,2,1} = S^0_{N,2,1} \exp[-\Sigma^{N-1}_{i=1} \mu_{i,2,1} \Delta x] \{\rho_{N,2,1}\} \exp[-\mu'_{N,1,1} \Delta y] \quad (14)$$

Since the $\rho$'s and the $\mu$'s were determined from the transmission and bottom-scattering measurements, in a fashion similar to that used for the (1,1)th row, side-scattering provides through the above equations the $\mu'$'s for the preceding row of voxels. The above procedure is to be repeated sequentially to determine, $\rho$, $\mu$ and $\mu'$s for each voxel. The ratios $\mu'/\rho$ and $\mu'/\mu$ provide Z-number information; if the incident scattering energies are chosen such that Compton scattering is dominant at the incident energy and the photoelectric effect is predominant at the scattering energy. If not, a few more iterations may be required to establish correspondence between $\rho$ and $\mu$. For the last row, farthest from the side-scatter detectors, no subsequent measurements are available to enable the determination of its $\mu'$'s. This problem can be overcome by artificially placing a material of known density, such as Lexan™ or Plexiglass™, in front of the last row and exposing it to the pencil beam, to provide additional side-scatter measurements without adding further unknowns. Alternatively, two sets of side-scatter detectors can be located on both sides of the luggage. This will not only solve the problem of determining the $\mu$'s of the last row, but also provides extra measurements that can be used to reduce the uncertainty in the evaluated parameters. The use of two sets of side-scatter detectors and/or top and bottom detectors can enable simultaneous processing of data as the scanning process progresses.

I claim:

1. A system for inspecting an object, comprising:
   a structure having a first, second and third orthogonal axes;
   a source of collimated x-ray pencil beam mounted to said structure along said first axis;
   an incident radiation detector mounted to said structure perpendicularly to said first axis;
   a first linear array of scattered radiation detectors mounted to said structure perpendicularly to said second axis;
   a second linear array of scattered radiation detectors mounted to said structure perpendicularly to said third axis;
   said source of collimated x-ray pencil beam, said incident radiation detector and said first and second linear arrays of scattered radiation detectors being spaced apart and defining therebetween an inspection zone; and
   means for moving an object relative to said source of collimated x-ray pencil beam, mounted to said structure in said inspection zone,
   such that radiation measurements available from said incident radiation detector and said first and second linear arrays of scattered radiation detectors when inspecting a voxel in an object in said inspection zone are indicative of incident radiation attenuation through said voxel, scattered radiation attenuation through said voxel and electron density of said voxel.

2. The system as claimed in claim 1, further comprising means for extracting volume imaging characteristics of an object in said inspection zone from measurements obtained from said incident radiation detector and said first and second linear array of scattered radiation detectors when a x-ray pencil beam is passed through said object.

3. A method for inspecting an object, comprising the steps of:
   defining and associating a first, second and third orthogonal axes with an object to be inspected;
   defining a voxel in said object;
   passing a x-ray beam through said voxel along said first axis;
   measuring incident radiation attenuation through said voxel along said first axis;
   while maintaining said x-ray beam aligned parallel with said first axis, sequentially moving said x-ray beam along each of said second and third axes, passing said x-ray beam through said object alongside said voxel, and measuring scattered radiation attenuation through said voxel along each of said second and third axes;
   relating said incident radiation attenuation and said scattered radiation attenuations to a material property of said voxel;
   such that said incident and scattered radiation attenuations and said material property are representative of an entirety of said voxel.

4. A method for inspecting an object, comprising the steps of:
   defining and associating a first, second and third orthogonal axes with an object to be inspected;
   defining a voxel in said object;
   passing an x-ray beam through said voxel along said first axis;
   measuring incident radiation attenuation through said voxel along said first axis;
   measuring scattered radiation attenuation through said voxel along said second axis;
   measuring scattered radiation attenuation through said voxel along said third axis;
   using measurements of incident radiation attenuation through said voxel along said first axis, scattered radiation attenuations through said voxel along said second and third axes, extracting volume imaging characteristics of said voxel along said first, second and third axes;
   such that volume details of said voxel are obtainable without rotating said object.

5. The method as claimed in claim 4, further including the step of using measurements of incident radiation attenuation through said voxel along said first axis, scattered radiation attenuations through said voxel along said second and third axes, verifying said incident radiation attenuation along said first axis.

* * * * *

UNITED STATES PATENT AND TRADEMARK OFFICE
CERTIFICATE OF CORRECTION

PATENT NO. : 6,556,653 B2
DATED : April 29, 2003
INVENTOR(S) : Esam Hussein

It is certified that error appears in the above-identified patent and that said Letters Patent is hereby corrected as shown below:

The cubical object shown in the illustrative figure and in FIG. 1 is made of straight lines only. The distortion appearing in the outline of the object is not to be considered as a part of the drawing.

Signed and Sealed this

Twenty-seventh Day of January, 2004

JON W. DUDAS
*Acting Director of the United States Patent and Trademark Office*